United States Patent [19]

Delledonne et al.

[11] Patent Number: 5,118,818
[45] Date of Patent: Jun. 2, 1992

[54] PROCESS FOR PREPARING ORGANIC CARBONATES

[75] Inventors: Daniele Delledonne, Oleggio; Franco Rivetti, Milan; Ugo Romano, Vimercate, all of Italy

[73] Assignee: Enichem Synthesis S.p.A., Palermo, Italy

[21] Appl. No.: 665,322

[22] Filed: Mar. 6, 1991

[30] Foreign Application Priority Data

| Mar. 9, 1990 [IT] | Italy | 19628 A/90 |
| Apr. 12, 1990 [IT] | Italy | 20012 A/90 |
| Jun. 4, 1990 [IT] | Italy | 20534 A/90 |

[51] Int. Cl.⁵ .................. C07D 307/89; C07C 69/96
[52] U.S. Cl. .................. 549/230; 549/228; 549/229; 558/260; 558/277
[58] Field of Search .......... 549/229, 230, 228; 558/260, 277

[56] References Cited

U.S. PATENT DOCUMENTS

| 3,846,468 | 11/1974 | Perrotti et al. | 558/260 |
| 4,218,391 | 8/1980 | Romano et al. | 558/260 |
| 4,318,862 | 3/1982 | Romano et al. | 558/277 |
| 4,361,519 | 11/1982 | Hallgren | 558/200 |
| 4,434,105 | 2/1984 | Buysch et al. | 558/260 |
| 4,436,668 | 3/1984 | Harder et al. | 558/260 |
| 4,604,242 | 8/1986 | Harley et al. | 558/260 |
| 4,658,041 | 4/1987 | Renfa | 558/260 |
| 4,785,130 | 11/1988 | Bhattacharya | 558/277 |
| 5,004,827 | 4/1991 | Curnutt | 558/260 |

FOREIGN PATENT DOCUMENTS 366177 5/1990 European Pat. Off. ............ 558/277

*Primary Examiner*—Cecilia Shen
*Attorney, Agent, or Firm*—Hedman, Gibson & Costigan

[57] ABSTRACT

Organic carbonates:

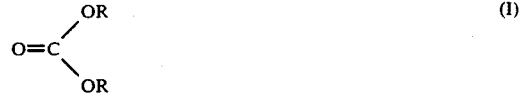

and cyclic organic carbonates:

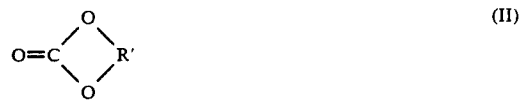

are prepared by reacting an alcohol (R—OH), or respectively a diol (HO—R'—OH), with carbon monoxide, in the presence of:
a halogen, or
a halogen and/or a halide ion and an oxidizing agent.

19 Claims, No Drawings

PROCESS FOR PREPARING ORGANIC CARBONATES

This invention relates to a process for preparing organic carbonates.

Organic carbonates are useful intermediates in the chemical sector, and of these dimethyl carbonate is widely used in the synthesis of other alkyl and aryl carbonates (used as plasticizers, synthetic lubricants, monomers for organic glasses etc.), in methylation and carbonylation reactions (for preparing urethanes, isocyanates, polycarbonates etc.), as a fuel additive and as an organic solvent.

The classical method of preparing alkyl carbonates is to react an alcohol with phosgene, as described for example in Kirk-Othmer, "Encyclopedia of Chemical Technology", 3rd edition, No. 4, page 758. This method involves numerous technical problems, as well as safety problems deriving from the use of phosgene.

To overcome these problems, alternative synthesis methods have been proposed, such as oxidative carbonylation of methanol in the presence of palladium catalysts (U.S. Pat. No. 4,361,519; Germany 3,212,535; GB 2,148,881).

The drawbacks of such a process are essentially the high catalyst cost, the co-production of oxalic acid esters [see Fenton, J. Org. Chem., 39, 701 (1974)] and the negative effect of the co-produced water, which even at low concentrations renders the catalyst ineffective.

Copper-based carbonylation catalysts have also been proposed (U.S. Pat. Nos. 3,846,468; 4,218,391; 4,318,862; 4,360,477), which however present problems deriving from the heterogeneousness of the reaction system and a certain sensitivity to water, this reducing the selectivity of carbon monoxide towards the formation of dimethyl carbonate and the reaction rate.

Other processes proposed in the art, but which have little practical importance, are the transesterification of other carbonates, the reaction of urea or urethanes with alcohols in the presence of catalysts, the reaction of alkyl halides or sulphates with alkaline carbonates, the reaction of alcohols with carbon dioxide and electrochemical synthesis.

It has now been found that dimethyl carbonate and other organic carbonates, including cyclic carbonates, can be prepared simply and conveniently, under mild conditions and with high yields, from an alcohol or diol and carbon monoxide, operating in the presence of a halogen or in the presence of a halogen and/or a halide ion and an oxidizing agent.

In accordance therewith the present invention provides a process for preparing an organic carbonate:

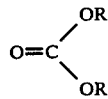  (I)

or a cyclic organic carbonate:

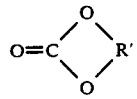  (II)

by reacting an alcohol R—OH, or respectively a diol HO—R'—OH, with carbon monoxide (CO), where:
R is a $C_1$-$C_{10}$ linear or branched alkyl radical; or a $C_5$-$C_8$ cycloalkyl radical; and
R' is a $C_2$-$C_5$ linear or branched alkylene radical; the process being characterised by conducting the reaction in the liquid phase at a temperature of between 25° and 200° C. under a carbon monoxide pressure of between 1 and 100 kg/cm$^2$, and:
in the presence of a halogen chosen from chlorine, bromine or iodine; or
in the presence of such a halogen and/or a corresponding halide ion and an oxidizing agent able to oxidize the halide ion to halogen.

In the preferred embodiment R—OH is chosen from methanol, ethanol, n-propanol, iso-propanol, n-butanol, iso-butanol, 2-ethylhexanol and cyclohexanol, so that R in formula (I) represents the methyl, ethyl, n-propyl, iso-propyl, n-butyl, iso-butyl, 2-ethylhexyl and cyclohexyl radical respectively. On this basis the organic carbonates (I) preferably prepared by the process of the present invention are dimethyl carbonate, diethyl carbonate, di-n-propyl carbonate, di-iso-propyl carbonate, di-n-butyl carbonate, di-iso-butyl carbonate, di-2-ethylhexyl carbonate and dicyclohexyl carbonate. In the most preferred embodiment dimethyl carbonate is prepared.

Again in the preferred embodiment the diol HO—R'—OH is ethylene glycol or propylene glycol, the cyclic carbonate (II) having the formula:

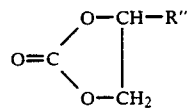

where R" is hydrogen or methyl respectively.

It is considered that the reactions involved in the formation of the organic carbonate (I) and of the cyclic organic carbonate (II) are respectively the following:

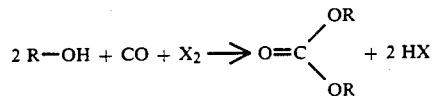

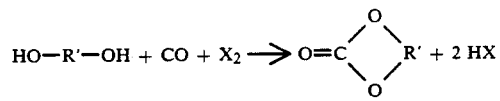

where X represents the halogen fed into the reaction environment or formed in situ by reaction between the halide ion and the oxidizing agent.

The preferred halogens are bromide and iodine, of which bromine is the more preferred.

The preferred halide ions are bromides and iodides, of which bromides are the more preferred. The halide ions can be the byproduct of the reaction between halogen, alcohol (or diol) and carbon monoxide, or can be supplied as such to the reaction environment. In particular the halide ions can be supplied in the form of hydrohalogen acids such as hydrobromic acid and hydroiodic acid, or in the form of metal halides, especially of alkaline or alkaline earth metals such as potassium halide or lithium bromide; or in the form of ammonium or phosphonium halides, such as those definable by the formulas $R'''_4N^+X^-$ and $R'''_4P^+X^-$ where $R'''$ indicates a hydrogen atom or an alkyl group.

The oxidizing agent able to oxidize the halide ion into halogen can be chosen from:
 (a) hydrogen peroxide, an organic percompound, N-bromosuccinimide, a nitrogen oxide, nitrous acid, nitric acid, a sulphur peracid, or a metal salt or an ester of said acids and peracids; or
 (b) an oxidizing system formed from oxygen and an oxygenated nitrogen compound chosen from nitrogen oxides, nitrous and nitric acids, and the salts or esters of said acids.

Of the oxidizing agents (a), the hydrogen peroxide is conveniently used in the form of an aqueous solution of a concentration of the order of 35-60% by weight. The organic percompounds can be chosen from organic peroxides, hydroperoxides and peresters, such as tert-butyl hydroperoxide and di-tert-butyl peroxide. Nitrogen oxides usable for this purpose are $NO_2$, ($N_2O_4$), $N_2O_3$ and $N_2O_5$. The nitric acid used is preferably nitric acid having a concentration of about 67% by weight or more, such as fuming nitric acid. The nitrate and nitrite salts usable for the purpose are preferably the salts of alkaline or alkaline earth metals or ammonium. The nitrous and nitric acid esters preferably used are the alkyl esters. An example of such esters is butyl nitrite. A sulphur peracid suitable for the purpose is peroxydisulphuric acid, preferably used in the form of an alkaline or alkaline earth metal salt. Finally, it has been found that N-bromosuccinimide acts as an oxidizing agent in the process of the present invention.

When the oxidizing system (b) is used, the oxygenated nitrogen compounds are conveniently chosen from NO, $NO_2$, ($N_2O_4$), $N_2O_3$ and $N_2O_5$. The nitric acid used is preferably nitric acid having a concentration of about 67% by weight or more, such as fuming nitric acid. The nitrate and nitrite salts usable for the purpose are preferably the salts of alkaline or alkaline earth metals or ammonium, or the salts of metals such as cerium and gallium, specific examples of which are sodium nitrite, cerium and ammonium nitrate and gallium nitrate. The nitrous and nitric acid esters preferably used are the alkyl esters. An example of such esters is butyl nitrite. When using the catalytic system (b), catalytic quantities of a halogen (or halide) and an oxygenated nitrogen compound are generally required. In this case the halide ion is oxidized to halogen by the oxygen in accordance with the equation:

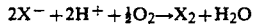
$$2X^- + 2H^+ + \tfrac{1}{2}O_2 \rightarrow X_2 + H_2O$$

The process for preparing organic carbonates according to the present invention is conducted by bringing the reactants into mutual contact operating in the liquid phase at a temperature generally between 25° and 200° C. under a carbon monoxide pressure generally between 1 and 100 kg/cm² for a time of between 1 and 240 minutes.

In the embodiment in which a halogen is used without an oxidizing agent, the process is conducted at a temperature of between 25° and 200° C. under a carbon monoxide pressure of between 1 and 100 kg/cm². The upper pressure limit is not critical and is dictated mainly by practical considerations. It has been found that the organic carbonate yield is a function of temperature, with optimum results between 50° and 150° C., and carbon monoxide pressure, the yield increasing as the pressure increases. The process can be carried out in an inert organic solvent with a halogen quantity stoichiometrically equivalent to the chosen alcohol or diol.

However in the preferred embodiment the alcohol or diol is used in excess over the stoichiometric, the excess serving as the reaction solvent. In practice a solution of the chosen halogen in an excess of alcohol or diol is prepared and the solution is placed under carbon monoxide and stirred at the above temperature, until the halogen has been completely or substantially completely converted. Under these conditions the reaction time can generally vary from 1 to 240 minutes and is typically of the order of 5-120 minutes. The reaction can be conducted in the presence of a base able to block the hydrohalogen acid which forms as a co-product of the reaction. The base can be a carbonate or bicarbonate of an alkaline or alkaline earth metal, such as sodium carbonate or bicarbonate, in stoichiometric or approximately stoichiometric quantity to the hydrohalogen acid developed. According to a particular embodiment, a metal, compound or complex of an element of group VIII of the periodic table is added to the reaction mixture as catalyst. The use of such a catalyst, usable also in supported form on an inert solid support if a metal, enables the reaction to be conducted under milder temperature and pressure conditions. The preferred elements of group VIII are palladium, rhodium and platinum, such as lithium and palladium chloride and platinum chloride. The compound or complex is preferably added in a quantity of 0.01-1 mol % on the halogen.

When the process of the present invention is conducted with a halogen and/or a halide ion, in the presence of the oxidizing agent (a), the halogen or halide ion concentration used is conveniently between $10^{-3}$ and 1 mole/liter and the oxidizing agent concentration between $10^{-1}$ and 5 moles/liter of alcohol, their mole ratio generally being between 1:100 and 1:1. The reaction is conducted at a temperature of between 25° and 200° C. under a carbon monoxide pressure of between 1 and 100 kg/cm² for a reaction time of between about 1 and about 240 minutes.

In the preferred embodiment, the halogen or halide ion concentration varies from $10^{-2}$ to 0.5 moles/liter, the oxidizing agent concentration varies from $10^{-1}$ to 2 moles/liter of alcohol, the molar ratio of halogen or halide ion to oxidizing agent varies from 1:50 to 1:1, the temperature varies from 50° to 120° C. and the carbon monoxide pressure varies from 2 to 100 kg/cm².

When the process of the present invention is conducted with a halogen and/or a halide ion, in the presence of the oxidizing system (b), the halogen or halide ion concentration used is conveniently between $10^{-3}$ and 2 moles/liter of alcohol and the oxygenated nitrogen compound concentration between $10^{-3}$ and 2 moles/liter of alcohol, their molar ratio not being critical but generally being between 500:1 and 0.002:1. The reaction is conducted at a temperature of between 25° and 200° C. under a total carbon monoxide plus oxygen pressure of between 1 and 100 kg/cm². The upper pressure limit is not critical and is dictated mainly by practical reasons. The ratio of oxygen partial pressure to carbon monoxide partial pressure in the gaseous mixture is not critical and can generally vary from 0.005:1 to 500:1. In the preferred embodiment, the halogen or halide ion concentration varies from $10^{-2}$ to 1 mole/liter of alcohol, the oxygenated nitrogen compound concentration varies from $10^{-2}$ to 1 mole/liter of alcohol, the molar ratio of halogen or halide ion to the oxygenated nitrogen compound varies from 50:1 to 0.02:1, the temperature varies from 50° to 120° C., the total oxygen plus carbon monoxide pressure varies from 2 to 100 kg/cm$^2$ and the ratio of oxygen partial pressure to carbon monoxide partial pressure varies from 0.01:1 to 1:1. Under these conditions the reaction time varies from about 1 to about 240 minutes. In a preferred embodiment a metal, compound or complex of an element of group VIII of the periodic table is added to the reaction mixture as catalyst to increase the reaction rate. The preferred elements of group VIII are palladium, rhodium and platinum, such as lithium and palladium chloride and platinum chloride. Such a catalyst is conveniently used in a quantity of 0.01–1 mol % on the halogen or halide ion.

In the preceding embodiments either pure carbon monoxide or mixtures containing carbon monoxide and other inert gases can be used. Likewise, when oxygen is required among the reactants, either pure oxygen or oxygen diluted with an inert gas such as nitrogen, for example air or oxygen-enriched air, can be used. In all cases, operating under the aforesaid conditions the organic carbonate is obtained with high yield and a high reaction rate. The organic carbonate produced in this manner can be separated from the reaction mixture by normal methods such as distillation or fractionation.

The process of the present invention can be conducted discontinuously (batchwise), semicontinuously or continuously. The following experimental examples are given to better illustrate the invention.

EXAMPLE 1

60 g of methanol and 3.25 g (20 mmoles) of bromine are introduced into a 250 ml pressure vessel lined internally with Teflon ® and fitted with a mechanical stirrer and heat transfer means. Carbon monoxide is fed into the pressure vessel to a pressure of 10 kg/cm$^2$. It is heated to 85° C. under stirring for 10 minutes. It is then cooled to ambient temperature, the gas vented and the liquid subjected to gaschromatography analysis.

A dimethyl carbonate yield of 17 mmoles (1.53 g) is determined, equal to 85% on the moles of bromine introduced. Methyl formate (11 mmoles) is formed as by-product.

EXAMPLE 2

60 g of methanol and 5.07 g (20 mmoles) of iodine are introduced into a 250 ml pressure vessel lined internally with Teflon ® and fitted with a mechanical stirrer and heat transfer means. Carbon monoxide is fed into the pressure vessel to a pressure of 10 kg/cm$^2$. It is heated to 110° C. under stirring for 1.5 hours. It is then cooled to ambient temperature, the gas vented and the liquid subjected to gaschromatography analysis.

A dimethyl carbonate yield of 1 mmole (0.09 g) is determined, equal to 5% on the moles of iodine introduced. Dimethoxymethane (1.5 mmoles) is formed as by-product.

EXAMPLE 3

60 g of methanol and 3.25 g (20 mmoles) of bromine are introduced into a 150 ml glass pressure vessel fitted with a mechanical stirrer and heat transfer means. Carbon monoxide is fed into the pressure vessel to a pressure of 3 kg/cm$^2$. It is heated to 50° C. under stirring for 60 minutes. It is then cooled to ambient temperature, the gas vented and the liquid subjected to gaschromatography analysis.

A dimethyl carbonate yield of 3.6 mmoles (0.32 g) is determined, equal to 18% on the moles of bromine introduced. Methyl formate (9 mmoles) is formed as by-product. Table 1 shows the results obtained in this example.

EXAMPLES 4 and 5

60 g of methanol, 3.25 g (20 mmoles) of bromine and 2.12 g (20 mmoles) of sodium carbonate are introduced into a 250 ml pressure vessel lined internally with Teflon ® and fitted with a mechanical stirrer and heat transfer means. Carbon monoxide is fed into the pressure vessel under the conditions shown in Table 1, which also shows the results obtained.

TABLE 1

| Example No. | 3 | 4 | 5 |
|---|---|---|---|
| Temp. (°C.) | 50 | 70 | 70 |
| P(CO) (kg/cm$^2$) | 3 | 10 | 40 |
| Time (min) | 60 | 30 | 25 |
| DMC (mmoles) | 3.6 | 14.6 | 15.6 |
| (grams) | 0.32 | 1.32 | 1.40 |
| (yield %) | 18 | 73 | 78 |
| HCOOMe (mmoles) | 9 | traces | traces |

DMC = dimethyl carbonate
HCOOme = methyl formate the DMC yield being evaluated on the moles of bromide introduced.

EXAMPLE 6

The procedure of example 4 is repeated, but replacing the sodium carbonate with 3.36 g (40 mmoles) of sodium bicarbonate. 6 mmoles (0.54 g) of dimethyl carbonate are obtained with a molar yield of 30% on the bromine.

EXAMPLE 7

60 g of methanol, 5.07 g (20 mmoles) of iodine and 2.12 g (20 mmoles) of sodium carbonate are introduced into a 250 ml pressure vessel lined internally with Teflon ® and fitted with a mechanical stirrer and heat transfer means. Carbon monoxide is fed into the pressure vessel to a pressure of 10 kg/cm$^2$. It is heated to 100° C. under stirring for 60 minutes. It is then cooled to ambient temperature, the gas vented and the liquid subjected to gaschromatography analysis.

A dimethyl carbonate yield of 11 mmoles (0.99 g) is determined, equal to 55% on the moles of iodine introduced.

EXAMPLE 8

60 g of ethanol and 3.25 g (20 mmoles) of bromine are introduced into a 250 ml pressure vessel lined internally with Teflon ® and fitted with a mechanical stirrer and heat transfer means. Carbon monoxide is fed into the pressure vessel to a pressure of 10 kg/cm$^2$. It is heated to 85° C. under stirring for 15 minutes. It is then cooled to ambient temperature, the gas vented and the liquid subjected to gaschromatography analysis.

A diethyl carbonate yield of 9 mmoles (1.06 g) is determined, equal to 45% on the moles of bromine introduced. Ethyl formate (4 mmoles) is formed as by-product.

EXAMPLE 9

60 g of methanol, 3.25 g (20 mmoles) of bromine, 13 mg (0.05 mmoles) of lithium palladium chloride (Li$_2$PdCl$_4$) and 2.12 g (20 mmoles) of sodium carbonate are introduced into a 150 ml glass pressure vessel fitted with a mechanical stirrer and heat transfer means. Carbon monoxide is fed into the pressure vessel to a pressure of 3 kg/cm$^2$. It is heated to 50° C. under stirring for 10 minutes. It is then cooled to ambient temperature, the gas vented and the liquid subjected to gaschromatography analysis. A dimethyl carbonate yield of 17.4 mmoles (1.57 g) is determined, equal to 87% on the moles of bromine introduced.

EXAMPLE 10

60 g of methanol, 5.04 g (20 mmoles) of iodine, 13 mg (0.05 mmoles) of lithium tetrachloropalladate (Li$_2$PdCl$_4$) and 2.12 g (20 mmoles) of sodium carbonate are introduced into a 250 ml glass pressure vessel lined internally with Teflon ® and fitted with a mechanical stirrer and heat transfer means. Carbon monoxide is fed into the pressure vessel to a pressure of 3 kg/cm$^2$. It is heated to 50° C. under stirring for 220 minutes. It is then cooled to ambient temperature, the gas vented and the liquid subjected to gaschromatography analysis.

A dimethyl carbonate yield of 17.3 mmoles (1.56 g) is determined, equal to 86% on the moles of iodine introduced.

EXAMPLE 11

91.7 g of ethylene glycol and 3.25 g (20 mmoles) of bromine are introduced into a 250 ml glass pressure vessel lined internally with Teflon ® and fitted with a mechanical stirrer and heat transfer means. Carbon monoxide is fed into the pressure vessel to a pressure of 10 kg/cm$^2$. It is heated to 85° C. under stirring for 15 minutes. It is then cooled to ambient temperature, the gas vented and the liquid subjected to gaschromatography analysis. An ethylene carbonate yield of 7 mmoles (0.62 g) is determined, equal to 35% on the moles of bromine introduced.

EXAMPLE 12

60 g of methanol, 1.0 g (6.25 mmoles) of bromine and 13 mg (0.05 mmoles) of lithium tetrachloropalladate (Li$_2$PdCl$_4$) are introduced into a 250 ml glass pressure vessel lined internally with Teflon ® and fitted with a mechanical stirrer and heat transfer means. Carbon monoxide is fed into the pressure vessel to a pressure of 10 kg/cm$^2$. It is heated to 100° C. under stirring for 20 minutes. It is then cooled to ambient temperature, the gas vented and the liquid subjected to gaschromatography analysis. A dimethyl carbonate yield of 5.74 mmoles (0.516 g) is determined, equal to 92% on the moles of bromine introduced.

EXAMPLE 13

60 g of methanol, 16 g (100 mmoles) of bromine and 10.6 g (100 mmoles) of sodium carbonate are introduced into a 250 ml glass pressure vessel lined internally with Teflon ® and fitted with a mechanical stirrer and heat transfer means. Carbon monoxide is fed into the pressure vessel to a pressure of 30 kg/cm$^2$. It is heated to 85° C. under stirring for 35 minutes. It is then cooled to ambient temperature, the gas vented and the liquid subjected to gaschromatography analysis.

A dimethyl carbonate yield of 64 mmoles (5.76 g) is determined, equal to 64% on the moles of bromine introduced.

EXAMPLE 14

60 g of methanol, 0.8 g (5 mmoles) of bromine and 31 mg (0.11 mmoles) of platinum chloride (PtCl$_2$) are introduced into a 250 ml glass pressure vessel lined internally with Teflon ® and fitted with a mechanical stirrer and heat transfer means. Carbon monoxide is fed into the pressure vessel to a pressure of 20 kg/cm$^2$. It is heated to 100° C. under stirring for 30 minutes. It is then cooled to ambient temperature, the gas vented and the liquid subjected to gaschromatography analysis.

A dimethyl carbonate yield of 4.7 mmoles (0.42 g) is determined, equal to 94% on the moles of bromine introduced.

EXAMPLE 15

40 g of methanol, 2.07 g (33 mmoles) of fuming nitric acid and 0.54 g (3.3 mmoles) of bromine are introduced into a 250 ml pressure vessel lined internally with Teflon ® and fitted with a mechanical stirrer and heat transfer means. Carbon monoxide and oxygen are fed into the pressure vessel to partial pressures of 20 and 5 kg/cm$^2$ respectively. It is heated to 110° C. under stirring for 30 minutes. It is then cooled to ambient temperature, the gas vented and the liquid subjected to gaschromatography analysis. A dimethyl carbonate yield of 6.0 g (67 mmoles) is determined.

EXAMPLE 16

40 g of methanol, 2.07 g (33 mmoles) of fuming nitric acid and 0.13 g (0.8 mmoles) of bromine are introduced into a 250 ml pressure vessel lined internally with Teflon ® and fitted with a mechanical stirrer and heat transfer means. Carbon monoxide and oxygen are fed into the pressure vessel to partial pressures of 20 and 5 kg/cm$^2$ respectively. It is heated to 100° C. under stirring for 180 minutes. It is then cooled to ambient temperature, the gas vented and the liquid subjected to gaschromatography analysis. A dimethyl carbonate yield of 4.85 g (54 mmoles) is determined.

EXAMPLE 17

60 g of methanol, 5.25 g (50 mmoles) of lithium nitrate dihydrate and 0.80 g (5 mmoles) of bromine are introduced into a 250 ml pressure vessel lined internally with Teflon ® and fitted with a mechanical stirrer and heat transfer means. Carbon monoxide and oxygen are fed into the pressure vessel to partial pressures of 10 and 5 kg/cm$^2$ respectively. It is heated to 100° C. under stirring for 180 minutes. It is then cooled to ambient temperature, the gas vented and the liquid subjected to gaschromatography analysis. A dimethyl carbonate yield of 1.29 g (14.3 mmoles) is determined.

EXAMPLE 18

40.8 g of methanol, 2.07 g (33 mmoles) of fuming nitric acid and 0.87 g (10 mmoles) of lithium bromide are introduced into a 250 ml pressure vessel lined internally with Teflon ® and fitted with a mechanical stirrer and heat transfer means. Carbon monoxide and oxygen are fed into the pressure vessel to partial pressures of 20 and 5 kg/cm$^2$ respectively. It is heated to 110° C. under stirring for 120 minutes. It is then cooled to ambient temperature, the gas vented and the liquid subjected to gaschromatography analysis. A dimethyl carbonate yield of 3.87 g (43 mmoles) is determined.

EXAMPLE 19

40 g of methanol, 3.07 g (5.6 mmoles) of ammonium cerium nitrate and 0.53 g (3.3 mmoles) of bromine are introduced into a 250 ml pressure vessel lined internally with Teflon ® and fitted with a mechanical stirrer and heat transfer means. Carbon monoxide and oxygen are fed into the pressure vessel to partial pressures of 20 and 5 kg/cm$^2$ respectively. It is heated to 100° C. under stirring for 210 minutes. It is then cooled to ambient temperature, the gas vented and the liquid subjected to gaschromatography analysis. A dimethyl carbonate yield of 2.97 g (33 mmoles) is determined.

EXAMPLE 20

40 g of methanol, 2.07 g (33 mmoles) of fuming nitric acid and 0.837 g (3.3 mmoles) of iodine are introduced into a 250 ml pressure vessel lined internally with Teflon ® and fitted with a mechanical stirrer and heat transfer means. Carbon monoxide and oxygen are fed into the pressure vessel to partial pressures of 20 and 5 kg/cm$^2$ respectively. It is heated to 100° C. under stirring for 100 minutes. It is then cooled to ambient temperature, the gas vented and the liquid subjected to gaschromatography analysis. A dimethyl carbonate yield of 2.80 g (31 mmoles) is determined.

EXAMPLE 21

40 g of methanol, 2.07 g (33 mmoles) of fuming nitric acid and 1.66 g (10 mmoles) of potassium iodide are introduced into a 250 ml pressure vessel lined internally with Teflon ® and fitted with a mechanical stirrer and heat transfer means. Carbon monoxide and oxygen are fed into the pressure vessel to partial pressures of 20 and 5 kg/cm$^2$ respectively. It is heated to 100° C. under stirring for 75 minutes. It is then cooled to ambient temperature, the gas vented and the liquid subjected to gaschromatography analysis. A dimethyl carbonate yield of 1.42 g (15.8 mmoles) is determined.

EXAMPLE 22

40 g of methanol, 3.07 g (5.6 mmoles) of $(NH_4)_2Ce(NO_3)_6$ and 0.87 g (10 mmoles) of lithium bromide are introduced into a 250 ml pressure vessel lined internally with Teflon ® and fitted with a mechanical stirrer and heat transfer means. Carbon monoxide and oxygen are fed into the pressure vessel to partial pressures of 20 and 5 kg/cm$^2$ respectively. It is heated to 100° C. under stirring for 150 minutes. It is then cooled to ambient temperature, the gas vented and the liquid subjected to gaschromatography analysis. A dimethyl carbonate yield of 0.23 g (2.5 mmoles) is determined.

EXAMPLE 23

50 g of ethanol, 2.07 g (33 mmoles) of fuming nitric acid and 0.54 g (3.3 mmoles) of bromine are introduced into a 250 ml pressure vessel lined internally with Teflon ® and fitted with a mechanical stirrer and heat transfer means. Carbon monoxide and oxygen are fed into the pressure vessel to partial pressures of 20 and 5 kg/cm$^2$ respectively. It is heated to 100° C. under stirring for 45 minutes. It is then cooled to ambient temperature, the gas vented and the liquid subjected to gaschromatography analysis. A diethyl carbonate yield of 1.21 g (15 mmoles) is determined.

EXAMPLE 24

50 g. of methanol, 0.15 g (2.1 mmoles) of sodium nitrite and 4.95 g (29 mmoles) of hydrobromic acid in 48 wt % aqueous solution are introduced into a 250 ml pressure vessel lined internally with Teflon ® and fitted with a mechanical stirrer and heat transfer means. Carbon monoxide and oxygen are fed into the pressure vessel to partial pressures of 20 and 7 kg/cm$^2$ respectively. It is heated to 71° C. under stirring for 135 minutes. It is then cooled to ambient temperature, the gas vented and the liquid subjected to gaschromatography analysis.

A dimethyl carbonate yield of 4.95 g (55 mmoles) is determined. Three successive additions each of 0.15 g (2.1 mmoles) of sodium nitrite are made, after each addition pressurizing with carbon monoxide and oxygen to partial pressures of 20 and 8 kg/cm$^2$ respectively, and heating to 70° C. for the time indicated in the following table, which also shows the results obtained in the three successive additions.

| Addition | 1st | 2nd | 3rd |
| --- | --- | --- | --- |
| Time (min) | 130 | 170 | 165 |
| DMC (mmoles) | 56 | 56 | 45 |
| (grams) | 5.04 | 5.4 | 4.05 |
| DMC total (mmoles) | 111 | 167 | 212 |
| (grams) | 9.99 | 15.03 | 19.02 |

DMC = dimethyl carbonate

EXAMPLE 25

55 g of methanol, 0.9 g (8.7 mmoles) of butyl nitrite and 4.95 g (29 mmoles) of hydrobromic acid in 48 wt % aqueous solution are introduced into a 250 ml pressure vessel lined internally with Teflon ® and fitted with a mechanical stirrer and heat transfer means. Carbon monoxide and oxygen are fed into the pressure vessel to partial pressures of 20 and 7 kg/cm$^2$ respectively. It is heated to 90° C. under stirring for 120 minutes. It is then cooled to ambient temperature, the gas vented and the liquid subjected to gaschromatography analysis.

A dimethyl carbonate yield of 8.91 g (99 mmoles) is determined.

EXAMPLE 26

55 g of methanol, 0.43 g (1.1 mmoles) of gallium trinitrate and 4.95 g (29 mmoles) of hydrobromic acid in 48 wt % aqueous solution are introduced into a 250 ml pressure vessel lined internally with Teflon ® and fitted with a mechanical stirrer and heat transfer means. Carbon monoxide and oxygen are fed into the pressure vessel to partial pressures of 20 and 7 kg/cm$^2$ respectively. It is heated to 80° C. under stirring for 140 minutes. It is then cooled to ambient temperature, the gas vented and the liquid subjected to gaschromatography analysis.

A dimethyl carbonate yield of 5.49 g (61 mmoles) is determined.

EXAMPLE 27

55.2 g of methanol, 0.15 g (2.1 mmoles) of sodium nitrite, 2.08 g (24 mmoles) of lithium bromide and 1.32 g (7.8 mmoles) of hydrobromic acid in 48 wt % aqueous solution are introduced into a 250 ml pressure vessel lined internally with Teflon ® and fitted with a mechanical stirrer and heat transfer means. Carbon monoxide and oxygen are fed into the pressure vessel to partial pressures of 20 and 7 kg/cm$^2$ respectively. It is heated to 80° C. under stirring for 140 minutes. It is then cooled to ambient temperature, the gas vented and the liquid subjected to gaschromatography analysis.

A dimethyl carbonate yield of 5.58 g (62 mmoles) is determined.

EXAMPLE 28

61.29 g of methanol, 5.68 g (75 mmoles) of $N_2O_3$ and 4.95 g (29 mmoles) of hydrobromic acid in 48 wt % aqueous solution are introduced into a 250 ml pressure vessel lined internally with Teflon ® and fitted with a mechanical stirrer and heat transfer means. Carbon monoxide and oxygen are fed into the pressure vessel to partial pressures of 20 and 7 kg/cm$^2$ respectively. It is heated to 85° C. under stirring for 240 minutes. It is then cooled to ambient temperature, the gas vented and the liquid subjected to gaschromatography analysis.

A dimethyl carbonate yield of 45.25 g (503 mmoles) is determined.

EXAMPLE 29

48.5 g of methanol, 1.43 g (19 mmoles) of $N_2O_3$ and 1.68 g (10 mmoles) of hydrobromic acid in 48 wt % aqueous solution are introduced into a 250 ml pressure vessel lined internally with Teflon ® and fitted with a mechanical stirrer and heat transfer means. Carbon monoxide and oxygen are fed into the pressure vessel to partial pressures of 20 and 7 kg/cm$^2$ respectively. It is heated to 80° C. under stirring for 75 minutes. It is then cooled to ambient temperature, the gas vented and the liquid subjected to gaschromatography analysis.

A dimethyl carbonate yield of 6.03 g (67 mmoles) is determined.

EXAMPLE 30

50 g of methanol, 1.37 g (18 mmoles) of $N_2O_3$, 1.68 g (10 mmoles) of hydrobromic acid in 48 wt % aqueous solution and 26.2 mg (0.1 mmoles) of lithium tetrachloropalladate ($Li_2PdCl_4$) are introduced into a 250 ml pressure vessel lined internally with Teflon ® and fitted with a mechanical stirrer and heat transfer means. Carbon monoxide and oxygen are fed into the pressure vessel to partial pressures of 20 and 7 kg/cm$^2$ respectively. It is heated to 80° C. under stirring for 20 minutes. It is then cooled to ambient temperature, the gas vented and the liquid subjected to gaschromatography analysis.

A dimethyl carbonate yield of 5.13 g (57 mmoles) is determined.

EXAMPLE 31

40 g of methanol, 2.07 g (33 mmoles) of fuming nitric acid and 0.54 g (3.3 mmoles) of bromine are introduced into a 250 ml pressure vessel lined internally with Teflon ® and fitted with a mechanical stirrer and heat transfer means. Carbon monoxide is fed into the pressure vessel to a pressure of 25 kg/cm$^2$. It is heated to 100° C. under stirring for 120 minutes. It is then cooled to ambient temperature, the gas vented and the liquid subjected to gaschromatography analysis.

A dimethyl carbonate yield of 2.88 g (32 mmoles) is determined.

EXAMPLE 32

60 g of methanol, 5.25 g (50 mmoles) of lithium nitrate dihydrate and 0.809 g (5.5 mmoles) of bromine are introduced into a 250 ml pressure vessel lined internally with Teflon ® and fitted with a mechanical stirrer and heat transfer means. Carbon monoxide is fed into the pressure vessel to a pressure of 10 kg/cm$^2$.

It is heated to 100° C. under stirring for 180 minutes. It is then cooled to ambient temperature, the gas vented and the liquid subjected to gaschromatography analysis. A dimethyl carbonate yield of 1.29 g (14.3 mmoles) is determined.

EXAMPLE 33

60 g of methanol, 9.71 g (100 moles) of hydrogen peroxide in a 35 wt % aqueous solution and 1.61 g (9.58 mmoles) of hydrobromic acid in 48 wt % aqueous solution are introduced into a 250 ml pressure vessel lined internally with Teflon ® and fitted with a mechanical stirrer and heat transfer means. Carbon monoxide is fed into the pressure vessel to a pressure of 30 kg/cm$^2$. It is heated to 80° C. under stirring for 75 minutes. It is then cooled to ambient temperature, the gas vented and the liquid subjected to gaschromatography analysis.

A dimethyl carbonate yield of 3.15 g (35 mmoles) is determined.

EXAMPLE 34

60 g of methanol, 9.00 g (80 mmoles) of tert-butyl hydroperoxide in an 80 wt % solution in di-tert-butyl peroxide and 1.76 g (10.5 mmoles) of hydrobromic acid in 48 wt % aqueous solution are introduced into a 250 ml pressure vessel lined internally with Teflon ® and fitted with a mechanical stirrer and heat transfer means. Carbon monoxide is fed into the pressure vessel to a pressure of 30 kg/cm$^2$. It is heated to 65° C. under stirring for 120 minutes. It is then cooled to ambient temperature, the gas vented and the liquid subjected to gaschromatography analysis. A dimethyl carbonate yield of 2.88 g (32 mmoles) is determined.

EXAMPLE 35

60 g of methanol, 12.2 g (51 moles) of sodium peroxydisulphate and 1.68 g (10 mmoles) of hydrobromic acid in 48 wt % aqueous solution are introduced into a 250 ml pressure vessel lined internally with Teflon ® and fitted with a mechanical stirrer and heat transfer means. Carbon monoxide is fed into the pressure vessel to a pressure of 30 kg/cm$^2$. It is heated to 110° C. under stirring for 105 minutes. It is then cooled to ambient temperature, the gas vented and the liquid subjected to gaschromatography analysis. A dimethyl carbonate yield of 1.35 g (15 mmoles) is determined.

EXAMPLE 36

70 g of methanol, 8.9 g (50 moles) of N-bromosuccinimide and 1.68 g (10 mmoles) of hydrobromic acid in 48 wt % aqueous solution are introduced into a 250 ml pressure vessel lined internally with Teflon ® and fitted with a mechanical stirrer and heat transfer means. Carbon monoxide is fed into the pressure vessel to a pressure of 30 kg/cm$^2$. It is heated to 70° C. under stirring for 120 minutes. It is then cooled to ambient temperature, the gas vented and the liquid subjected to gaschromatography analysis.

A dimethyl carbonate yield of 4.23 g (47 mmoles) is determined.

We claim:

1. A process for preparing an organic carbonate of the formula:

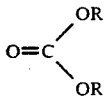

or a cyclic organic carbonate of the formula:

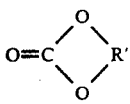

comprising reacting an alcohol R—OH, or respectively a diol HO—R'—OH, with carbon monoxide (CO), wherein:
R is a $C_1$-$C_{10}$ linear or branched alkyl radical; or a $C_5$-$C_8$ cycloalkyl radical; and
R' is a $C_2$-$C_5$ linear or branched alkylene radical; and wherein said reaction is conducted in the liquid phase at a temperature ranging from 25° to 200° C. under a carbon monoxide pressure ranging from 1 to 100 kg/cm$^2$, and
in the presence of a halogen selected from the group consisting of chlorine, bromine and iodine; or
in the presence of such a halogen and/or a corresponding halide ion and an oxidizing agent able to oxidize the halide ion to halogen.

2. A process as claimed in claim 1, wherein R—OH is selected from the group consisting of methanol, ethanol, n-propanol, iso-propanol, n-butanol, iso-butanol, 2-ethylhexanol and cyclohexanol.

3. A process as claimed in claim 2, wherein R—OH comprises methanol.

4. A process as claimed in claim 1, wherein said halogen is selected from the group consisting of bromine and iodine.

5. A process as claimed in claim 4, wherein said halogen comprises bromine.

6. A process as claimed in claim 1, wherein said halide is selected from the group consisting of bromide and iodide.

7. A process as claimed in claim 6, wherein said halide comprise bromide.

8. A process as claimed in claim 1, wherein said oxidizing agent is selected from the group consisting of hydrogen peroxide, tert-butyl hydroperoxide, di-tert-butyl hydroperoxide, N-bromosuccinimide, a nitrogen oxide, nitrous acid, nitric acid, a sulfur peracid, an alkaline metal, an alkaline earth metal, an ammonium salt of an alkaline metal, an ammonium salt of an alkaline earth metal, an ester of nitric acid, an ester of nitrous acid, an ester of sulfur peracid, and a combination of oxygen and oxygenated compounds selected from the group consisting of nitrogen oxides, nitrous or nitric acids and alkaline metals, alkaline earth metals or ammonium salts of alkaline metals, ammonium salts of alkaline earth metals, alkyl esters of alkaline metals and alkyl ester of alkaline earth metals.

9. A process as claimed in claim 8, wherein said oxidizing agent is selected from the group consisting of hydrogen peroxide having a concentration of 35-60% by weight, $NO_2$, $N_2O_4$, $N_2O_3$, $N_2O_5$, nitric acid having a concentration of at least about 67% by weight, and nitrate and nitrite salts of ammonium, cerium and gallium.

10. A process as claimed in claim 8, wherein said oxidizing agent is selected from the group consisting of NO, $NO_2$, $N_2O_4$, $N_2O_3$, $N_2O_5$, nitric acid having a concentration of about 67% by weight, and nitrate and nitrite salts of ammonium, cerium and gallium.

11. A process as claimed in claim 1 wherein halogen is used in the absence of an oxidizing agent, and operating at a temperature ranging from 25° to 200° C. under a carbon monoxide pressure ranging from 1 to 100 kg/cm$^2$ for a reaction time of between 1 and 240 minutes.

12. A process as claimed in claim 11 wherein the temperature ranges from 50° to 150° C. and the reaction time ranges from 5 to 120 minutes.

13. A process as claimed in claim 11 further comprising operating in the presence of a base which is able to block the formation of hydrohalogen acid reaction co-products.

14. A process as claimed in claim 11 further comprising operating in the presence of a catalyst selected from metal compounds or complexes of an element of group VIII of the period table.

15. A process as claimed in claim 1, wherein said reaction uses a halogen and/or halide ion in the presence of said oxidizing agent operating at a halogen or halide ion concentration ranging from $10^{-3}$ to 1 mole/liter and an oxidizing agent concentration ranging from $10^{-1}$ to 5 moles/liter of alcohol, with a mole ratio of halogen or halide ion to oxidizing agent ranging from 1:100 to 1:1, at a temperature ranging from 25° to 200° C. under a carbon monoxide pressure ranging from 1 to 100 kg/cm$^2$ for a reaction time ranging from 1 to 240 minutes.

16. A process as claimed in claim 15, wherein said halogen or halide ion concentration ranges from $10^{-2}$ to 0.5 moles/liter, the oxidizing agent concentration ranges from $10^{-1}$ to 2 moles/liter of alcohol, the molar ratio of halogen or halide ion to oxidizing agent ranges from 1:50 to 1:1, the temperature ranges from 50° to 120° C. and the carbon monoxide pressure ranges from 2 to 100 kg/cm$^2$.

17. A process as claimed in claim 1, wherein a halogen and/or a halide ion is used in the presence of an oxidizing agent comprising an oxygenated nitrogen compound operating at a halogen or halide ion concentration ranging from $10^{-3}$ to 2 moles/liter of alcohol and an oxygenated nitrogen compound concentration ranging from $10^{-3}$ to 2 moles/liter of alcohol, the molar ratio of halogen or halide ion to oxygenated nitrogen compound ranging from 500:1 to 0.002:1, at a temperature ranging from 25° to 200° C. under a total carbon monoxide plus oxygen pressure ranging from 1 to 100 kg/cm$^2$ and with a ratio of oxygen partial pressure to carbon monoxide partial pressure ranging from 0.005:1 to 500:1.

18. A process as claimed in claim 17, wherein the halogen or halide ion concentration ranges from $10^{-2}$ to 1 mole/liter of alcohol, the oxygenated nitrogen compound concentration ranges from $10^{-2}$ to 1 mole/liter of alcohol, the molar ratio of halogen or halide ion to the oxygenated nitrogen compound ranges from 50:1 to 0.02:1, the temperature ranges from 50° to 120° C., the total oxygen plus carbon monoxide pressure ranges from 2 to 100 kg/cm$^2$, the ratio of oxygen partial pressure to carbon monoxide partial pressure ranges from 0.01:1 to 1:1, and the reaction time ranges from 1 to 240 minutes.

19. A process as claimed in claim 17 further comprising operating in the presence of a catalyst selected from metals, compounds or complexes of an element of group VIII of the periodic table.

* * * * *